US012374003B2

(12) United States Patent
Sarti et al.

(10) Patent No.: US 12,374,003 B2
(45) Date of Patent: Jul. 29, 2025

(54) METHOD OF METAL ARTEFACT REDUCTION IN X-RAY DENTAL VOLUME TOMOGRAPHY

(71) Applicants: DENTSPLY SIRONA Inc.; SIRONA DENTAL SYSTEMS GMBH, Bensheim (DE)

(72) Inventors: Christina Sarti, Frankfurt (DE); Kai Stannigel, Weinheim (DE); Michael Elvers, Darmstadt (DE)

(73) Assignee: Dentsply Sirona Inc., York, PA (US)

( * ) Notice: Subject to any disclaimer, the term of this patent is extended or adjusted under 35 U.S.C. 154(b) by 358 days.

(21) Appl. No.: 17/604,045

(22) PCT Filed: Apr. 17, 2020

(86) PCT No.: PCT/EP2020/060864
§ 371 (c)(1),
(2) Date: Oct. 15, 2021

(87) PCT Pub. No.: WO2020/212573
PCT Pub. Date: Oct. 22, 2020

(65) Prior Publication Data
US 2022/0207794 A1  Jun. 30, 2022

(30) Foreign Application Priority Data
Apr. 18, 2019 (EP) .................................. 19170279

(51) Int. Cl.
*G06T 11/00* (2006.01)
(52) U.S. Cl.
CPC ........ *G06T 11/005* (2013.01); *G06T 2210/41* (2013.01)
(58) Field of Classification Search
CPC .............. G06T 11/005; G06T 2210/41; G06T 2211/441; G06T 2211/448; A61B 6/032;
(Continued)

(56) References Cited

U.S. PATENT DOCUMENTS 11,426,261 B2 * 8/2022 Hansson .............. A61C 8/0025
11,426,332 B2 * 8/2022 Banasiak ............... A61K 6/802
(Continued)

FOREIGN PATENT DOCUMENTS

CN    101777177 A    7/2010
CN    104093361 A    10/2014
(Continued)

OTHER PUBLICATIONS

International Search Report; PCT/EP2020/060864; May 29, 2020 (completed); Jun. 9, 2020 (mailed).
(Continued)

*Primary Examiner* — Andrae S Allison
(74) *Attorney, Agent, or Firm* — SCHWEGMAN LUNDBERG & WOESSNER, P.A.

(57) ABSTRACT

The present invention relates to a method of metal artefact reduction in x-ray dental volume tomography, the method comprising: a step (S1) of obtaining two-dimensional x-ray images (1) or a sinogram (2) of at least part (v) of a patient jaw (3a), acquired through relatively rotating an x-ray source (4) and a detector (5) around the patient jaw (3a); the method being characterized by further comprising: a step (S2) of detecting metal objects (6) in the two-dimensional x-ray images (1) or the sinogram (2) by using at least a trained artificial intelligence algorithm to generate 2D masks (7) which represent the metal objects (6) in the two-dimensional x-ray images (1) or 3D masks which represent the metal objects (6) in the sinogram (2), respectively; and a step (S4; S5) of reconstructing a three dimensional tomographic image (8) respectively based on two-dimensional x-ray images (1) or the sinogram (2) and the 2D masks (7) or the 3D masks as generated.

16 Claims, 9 Drawing Sheets

(58) Field of Classification Search
CPC ....... A61B 6/12; A61B 6/5205; A61B 6/5258; A61B 6/14
See application file for complete search history.

(56) References Cited

U.S. PATENT DOCUMENTS

| | | | |
|---|---|---|---|
| 11,806,206 | B2* | 11/2023 | Lowe ............... A61C 7/008 |
| 2008/0165920 | A1 | 7/2008 | De Man |
| 2011/0007956 | A1* | 1/2011 | Meyer ............ A61B 6/4441 382/131 |
| 2017/0000430 | A1* | 1/2017 | Lu .................. A61B 6/032 |
| 2018/0137658 | A1* | 5/2018 | Zhang ............. G06T 11/008 |
| 2018/0293762 | A1* | 10/2018 | Fu ................... G06T 11/006 |
| 2018/0374245 | A1 | 12/2018 | Xu |
| 2019/0108441 | A1* | 4/2019 | Thibault .......... G06T 11/003 |
| 2019/0328348 | A1* | 10/2019 | De Man ........... G06T 5/40 |

FOREIGN PATENT DOCUMENTS

| | | |
|---|---|---|
| CN | 107714069 A | 2/2018 |
| CN | 109419521 A | 3/2019 |
| EP | 3725229 | 10/2020 |
| JP | 2013233168 A | 11/2013 |
| JP | 2022530298 A | 6/2022 |
| JP | 7577663 B2 | 10/2024 |
| JP | 2024164073 A | 11/2024 |
| WO | 2018126396 | 7/2018 |
| WO | 2018126396 A1 | 7/2018 |
| WO | 2020212573 | 10/2020 |

OTHER PUBLICATIONS

International Preliminary Report on Patentability; PCT/EP2020/060864; May 29, 2020 (completed); Jun. 9, 2020 (mailed).
Written Opinion of the International Searching Authority; PCT/EP2020/060864; May 29, 2020 (completed); Jun. 9, 2020 (mailed).
Ghani et al.; "Deep Learning Based Sinogram Correction for Metal Artifact Reduction"; IS&T International Symposium on Electronic Imaging; vol. 2018, No. 15; Jan. 28, 2018; pp. 472-1-472-7.
Seemeen et al.; "Segmentation of artifacts and anatomy in CT metal artifact reduction"; Medical Physics, AIP, Melville, NY; vol. 39, No. 10; Oct. 1, 2012; pp. 5857-5868.
Wouter et al.; "Development and validation of segmentation and interpolation techniques in sinograms for metal artifact suppression in CT"; Medical Physics, AIP, Melville, NY; vol. 37, No. 2; pp. 620-628.
Karssemeijer et al.; "A stochastic model for automated detection of calcifications in digital mammograms"; Jul. 1, 1991; Information Processing in Medical Imaging, Springer Berlin Heidelberg; pp. 227-238.
Zhang Yanbo et al.; "Reduction of metal artifacts in x-ray CT images using a convolutional neural network"; Proceedings of Spie; vol. 10391, Sep. 25, 2017; pp. 103910V-103910V.
Chinese Office Action dated Feb. 29, 2024.
Japanese Office Action dated Feb. 9, 2024.
"European Application Serial No. 19170279.4, Extended European Search Report mailed Sep. 26, 2019", 8 pgs.
"European Application Serial No. 19170279.4, Communication Pursuant to Article 94(3) EPC mailed Jun. 23, 2022", 6 pgs.
"European Application Serial No. 19170279.4, Summons to Attend Oral Proceedings mailed Nov. 23, 2023", 4 pgs.
"European Application Serial No. 19170279.4, Response filed Apr. 21, 2021 to Extended European Search Report mailed Sep. 26, 2019", 31 pgs.
"European Application Serial No. 19170279.4, Response filed Jan. 2, 2023 to Communication Pursuant to Article 94(3) EPC mailed Jun. 23, 2022", 7 pgs.
"European Application Serial No. 19170279.4, Response filed Sep. 27, 2024 to Summons to Attend Oral Proceedings mailed Nov. 23, 2023", 35 pgs.
"European Application Serial No. 19170279.4, Communication Pursuant to Rule 114(2) EPC mailed Jan. 23, 2025", 14 pgs.
"European Application Serial No. 20718334.4, Noting of loss of rights pursuant to Rule 112(1) EPC mailed Dec. 9, 2021", 2 pgs.
"Japanese Application Serial No. 2021-540231, Decision of Refusal mailed Jun. 11, 2024", w/ English Translation, 6 pgs.
"Japanese Application Serial No. 2021-540231, Notification of Reasons for Refusal mailed Feb. 6, 2024", w/ English Translation, 6 pgs.
"Japanese Application Serial No. 2021-540231, Response filed Apr. 4, 2024 to Notification of Reasons for Refusal mailed Feb. 6, 2024", w/ English Translation, 16 pgs.
"Japanese Application Serial No. 2021-540231, Response filed Aug. 14, 2024 to Decision of Refusal mailed Jun. 11, 2024", w/ English Claims, 15 pgs.
Park, et al., "Sinogram-consistency learning in CT for metal artifact reduction", arXiv.1708.00607, (2017), 7 pgs.

\* cited by examiner

METHOD OF METAL ARTEFACT REDUCTION IN X-RAY DENTAL VOLUME TOMOGRAPHY

TECHNICAL FIELD OF THE INVENTION

The present invention relates to x-ray dental volume tomography (DVT). The present invention more particularly relates to a method of metal artefact reduction (MAR) in x-ray dental volume tomography.

BACKGROUND ART OF THE INVENTION

Figure 1:
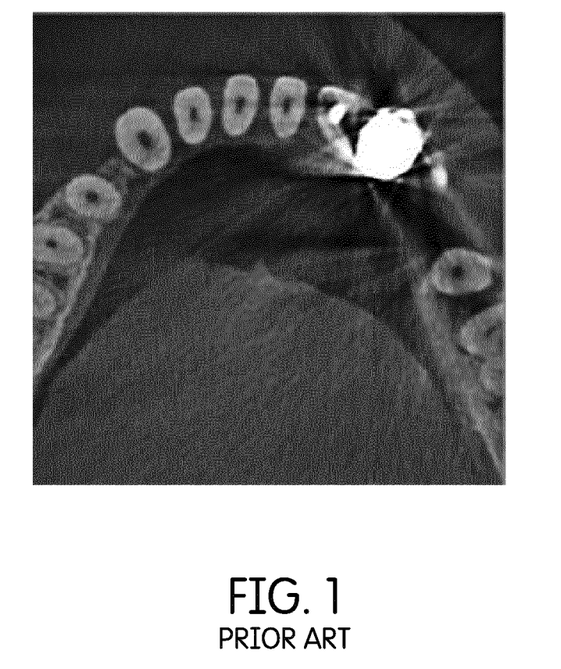
Figure 2:
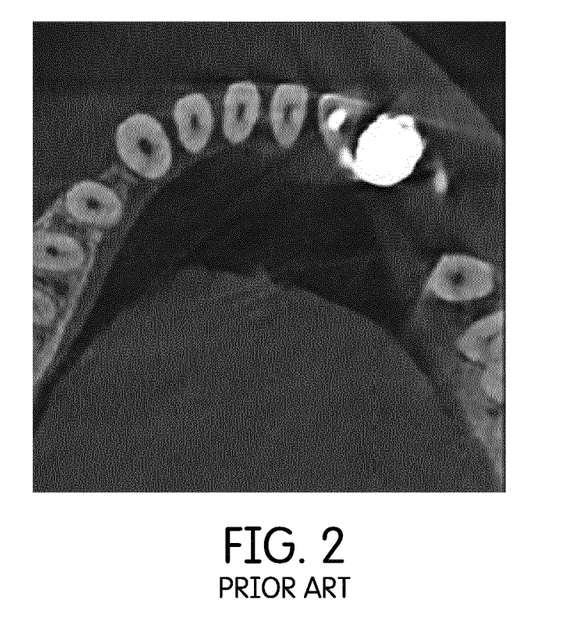
FIG. 2—is a tomogram corresponding to the same section in FIG. 1 reconstructed with the metal artefact reduction method according to the prior art as shown in FIG. 3.
Figure 3:
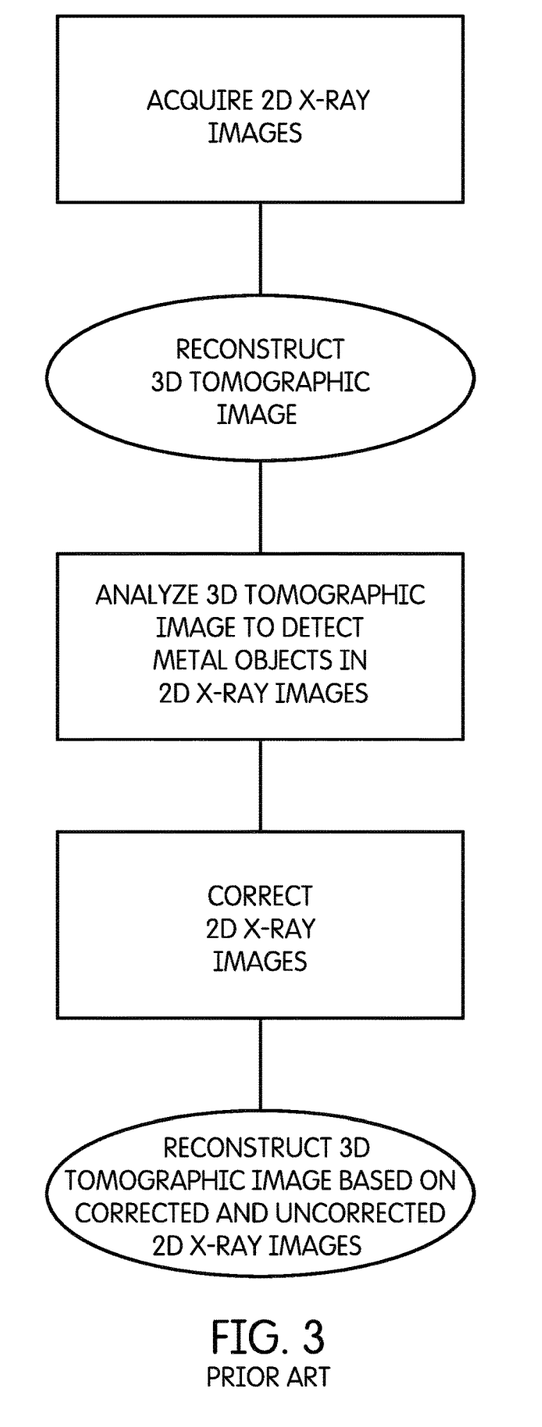
FIG. 3—is a flowchart showing the steps of a metal artefact reduction method according to the prior art.

In x-ray dental volume tomography, a three-dimensional (3D) tomographic image of the patient jaw is reconstructed based on two-dimensional (2D) x-ray images. Metal objects such as metallic fillings or implants in the patient's mouth can cause metal artefacts in the final three-dimensional tomographic image. The metal artefacts appear as dark or light stripes as shown in FIG. 1. These artefacts can complicate the medical diagnosis. A conventional method of metal artifact reduction is shown in FIG. 3. In the conventional method, first the two-dimensional x-ray images are acquired and subsequently used to reconstruct a three-dimensional (3D) tomographic image. Thereafter, the locations of the metal objects in the two-dimensional x-ray images are determined through a time-consuming analysis of the three-dimensional tomographic image. Knowing the locations of the metal objects, subsequently the metal artefacts in the two-dimensional x-ray images are corrected through classical image processing. Finally, a metal artifact-reduced three-dimensional tomographic image is reconstructed based on the corrected and uncorrected two-dimensional x-ray images. FIG. 2 shows a tomogram in which the metal artefacts in FIG. 1 have been reduced through the method in FIG. 3.

Figure 6:
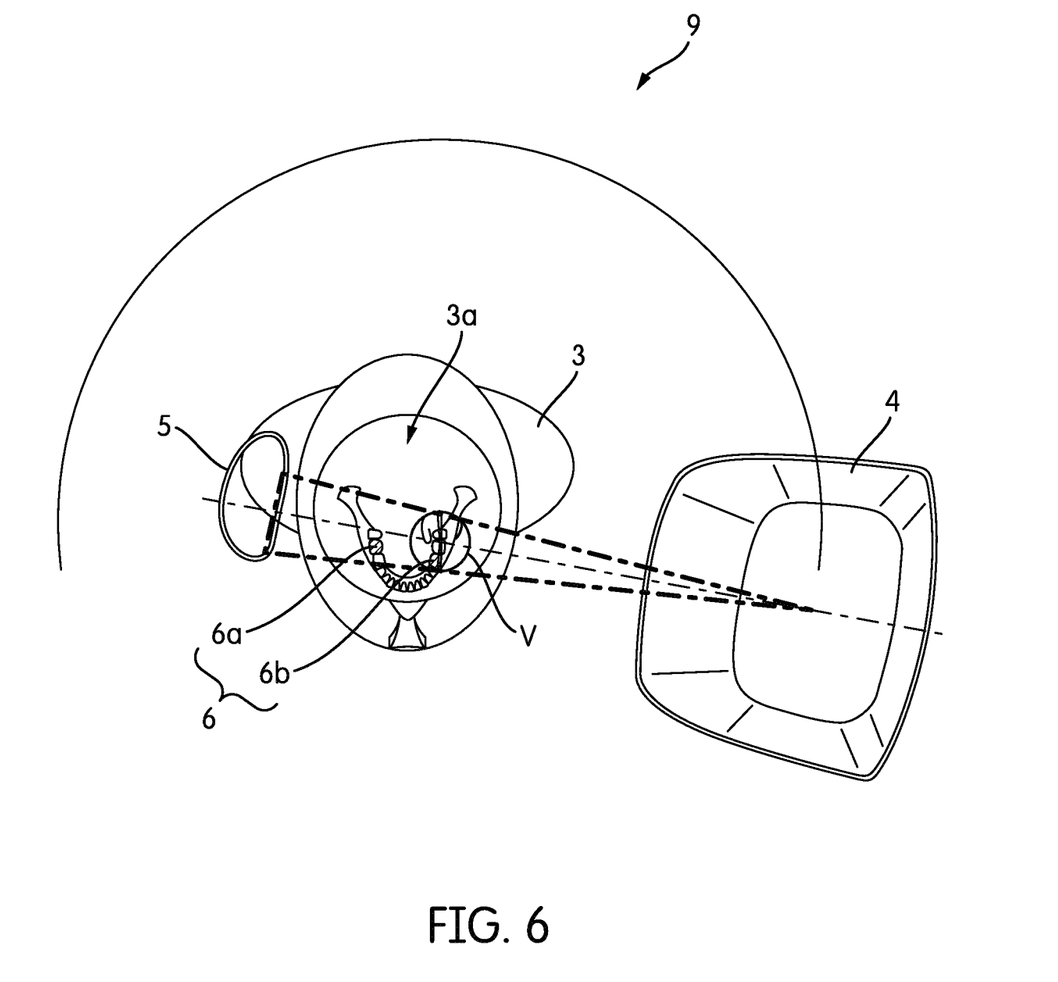
FIG. 6—is a schematic cross sectional top view of the x-ray unit of the x-ray dental volume tomography system according to the present invention.
Figure 7:
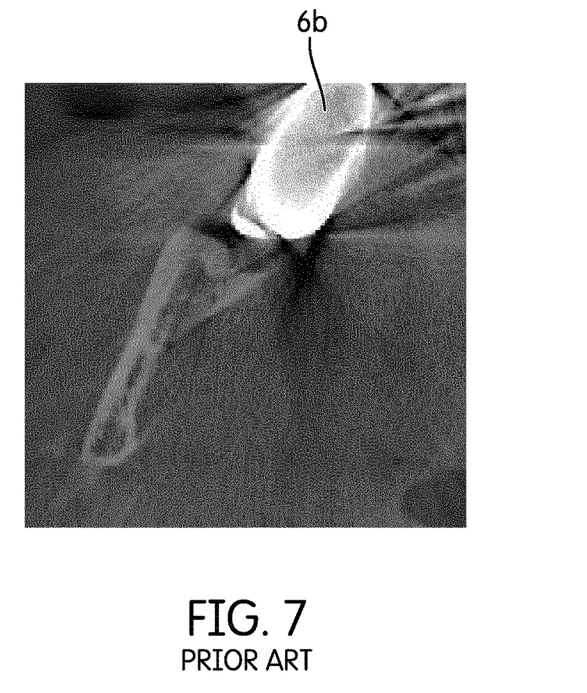
FIG. 7—is a tomogram according to the prior art with metal artefacts that are caused by metal objects outside the reconstructed volume.
Figure 8:
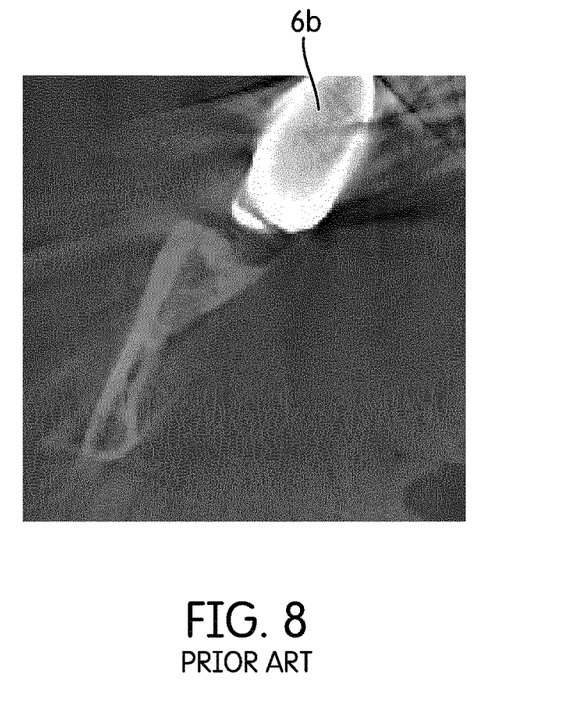
FIG. 8—is a tomogram corresponding to the same section in FIG. 7 reconstructed with a metal artefact reduction method according to the prior art as shown in FIG. 3.

In many situations, only a part (V) i.e., a small volume, of the patient jaw (3a) as shown in FIG. 6, is relevant to the diagnosis. In this case, only such small volume (V) of the patient jaw (3a) is irradiated from all angles and reconstructed. The remaining part of the patient jaw (3a) is not irradiated from all angles and is only seen in some of the acquired two-dimensional x-ray images and is not reconstructed. These two-dimensional x-ray images can cause metal artifacts in the final three-dimensional tomographic image as shown in FIG. 7 if there are metallic objects (6a) outside the small volume (V) to be reconstructed as shown in FIG. 6, even when such small volume (V) would not contain any metal object (6b). FIG. 8 is a tomogram corresponding to the same section in FIG. 7 and has been reconstructed with the metal artefact reduction method according to the prior art as shown in FIG. 3. The metal artefacts in FIG. 7 caused by the metal objects (6a) outside the small volume (V) cannot be corrected through the conventional method of metal artifact reduction shown in FIG. 3, and thus, the conventional metal artifact reduction method is not reliable.

Figure 4:
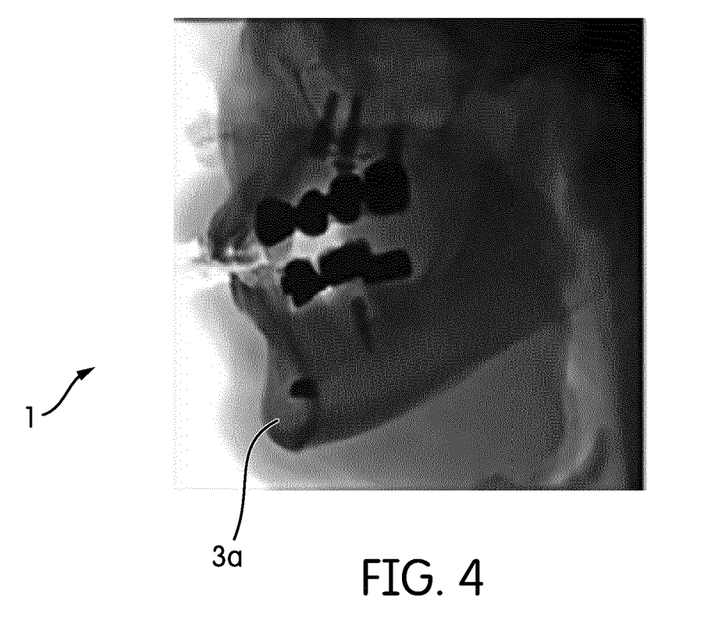
FIG. 4—is a two-dimensional x-ray image acquired with an x-ray unit according to the present invention.
Figure 5A:
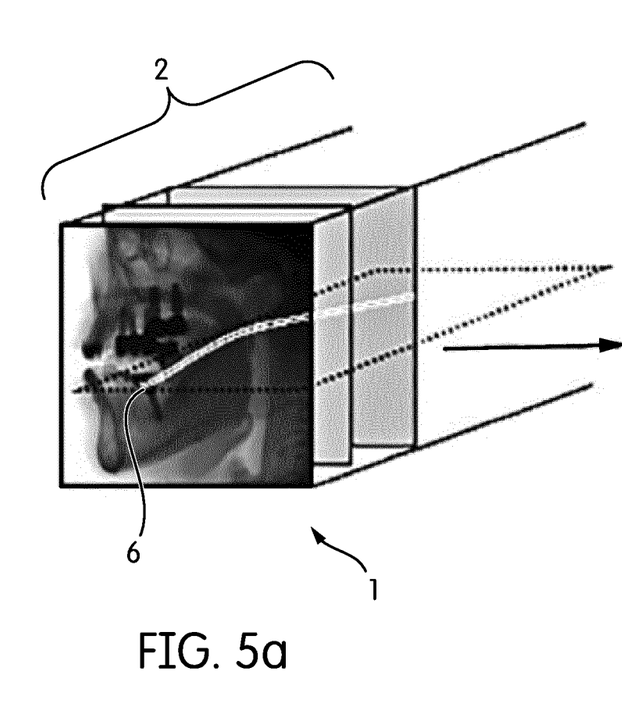
FIG. 5a—is a sinogram of two-dimensional x-ray images acquired with the x-ray unit according to the present invention.
Figure 5B:
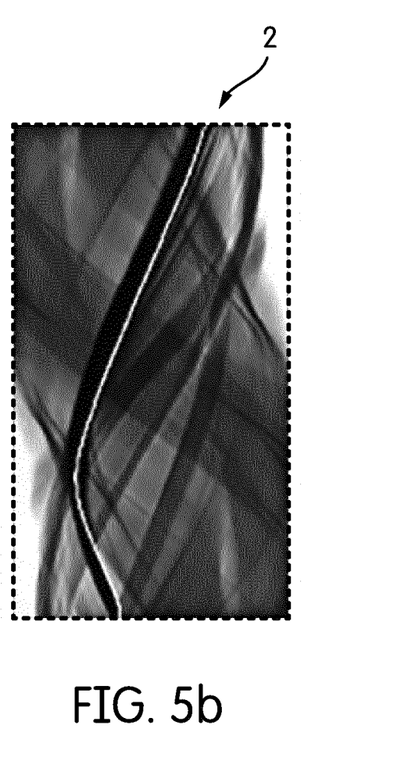
FIG. 5b—is a cross sectional view of the sinogram in FIG. 5a, when viewed along the vertical direction.

To avoid the above-mentioned first reconstruction step in the conventional method of FIG. 3, and to prevent artifacts due to metal objects (6a) located outside the small volume (V) to be reconstructed, the detection of metal objects may be directly performed on the two-dimensional x-ray images. For this purpose, the two dimensional-x-ray images or alternatively the sinogram can be analyzed. A two-dimensional x-ray image represents the projection of the irradiated three-dimensional object, for instance, a patient jaw as shown in FIG. 4. A sinogram is created when these projections taken at all angles are combined into an array of projections as shown in FIG. 5a. The trace of a metal object imaged over time defines curves in the sinogram as shown in FIGS. 5a and 5b. For the detection of the metal objects in the two-dimensional x-ray images, classical image processing methods such as thresholding, edge detection may be used. However, due to other dense structures such as bones or dentins, it is difficult to achieve a reliable detection of the metal objects. The dense structures may be erroneously recognized as metal objects. The converse may also happen, and the metal objects with lower density may not be detected. In such cases, the metal artifact reduction based on classical image processing of the two-dimensional x-ray images may not be reliably achieved.

In the two-dimensional x-ray images, at the places where the metal objects are located, the data for reconstructing a 3D artifact-free tomographic image is generally missing. In the approach disclosed in WO2018/126396A1 artificial intelligence is used to supplement the two-dimensional x-ray images where the data is missing. The sites including the missing data are initially determined through thresholding and subsequently supplemented with a trained artificial intelligence to reconstruct a metal artifact reduced three-dimensional tomographic image. However also this approach is prone to the disadvantages of the above-mentioned classical image processing techniques involving the use of thresholding.

DISCLOSURE OF THE INVENTION

An objective of the present invention is to overcome the above-mentioned disadvantages of the prior art and to provide a method of metal artefact reduction in x-ray dental volume tomography.

This objective has been achieved by the metal artefact reduction method as defined in claim 1, and the x-ray dental volume tomography system as defined in claim 10. The subject-matters of the dependent claims relate to further developments.

The present invention provides a method of metal artefact reduction in x-ray dental volume tomography. The method comprises: a step of obtaining two-dimensional x-ray images or a sinogram of at least part of a patient jaw, acquired through relatively rotating an x-ray source and a detector around the patient jaw; a step of detecting metal objects in the two-dimensional x-ray images or the sinogram by using a trained artificial intelligence algorithm to generate 2D masks which represent the metal objects in the two-dimensional x-ray images or 3D masks which represent the metal objects in the sinogram, respectively; and a step of reconstructing a three dimensional tomographic image respectively based on two-dimensional x-ray images or the sinogram and the 2D masks or the 3D masks as generated.

A major advantageous effect of the present invention is that the metal objects can be more reliably detected through directly and solely analyzing the 2D x-ray images or the sinogram by using 2D/3D masks that are generated through the trained artificial intelligence algorithm. Thereby, the need for initially reconstructing and analyzing the 3D tomographic image with metal objects can be obviated, and thus the process time can be comparatively shortened, and the process load can be comparatively reduced. Hence, the speed of reconstructing a metal artefact reduced 3D tomographic images has been improved. Another major advantageous effect of the present invention is that metallic objects that are not in the reconstructed volume can be reliably detected, and the metal artifacts caused by these metallic objects can be reduced. Thus, the metal artefact reduction method of the present invention has an improved tomographic image quality independently from the size of the volume to be reconstructed. Another major advantageous effect of the present invention is that the artificial intelligence algorithm can be continually trained with the help of real/virtual data including 2D x-ray images taken from the patient jaw or a calibration body from various angles, and thus the generation of 2D/3D mask for detecting the metal objects can be accordingly improved through such training. Thereby, the medical diagnosis can be increasingly facilitated.

According to the present invention, the three-dimensional tomographic image may be reconstructed in two alternative ways. In the first alternative, the method further comprises a step of correcting the two-dimensional x-ray images or the sinogram by means of the generated 2D masks or the 3D masks respectively, wherein in the reconstruction step, the three-dimensional tomographic image is reconstructed based on the corrected two-dimensional x-ray images or the corrected sinogram. In the second alternative, in the reconstruction step the three-dimensional tomographic image is reconstructed respectively based on the two-dimensional x-ray images or the sinogram as originally obtained and the 2D masks or the 3D masks as generated.

According to the present invention, the 2D/3D masks are preferably 2D/3D binary masks. Alternatively, probability masks or confidence masks may be used.

According to the present invention, the two-dimensional x-ray images or the sinogram may be corrected through classical image processing. Alternatively, another artificial intelligence algorithm may be used for correcting the two-dimensional x-ray images. This artificial intelligence algorithm can be trained with two-dimensional x-ray images data acquired from different patient jaws.

According to the present invention, the reconstruction of the three-dimensional tomographic image may be based solely on the corrected two-dimensional x-ray images or the corrected sinogram such that the metal objects are not present in the final three-dimensional tomographic image. Alternatively, the reconstruction of the three-dimensional tomographic image may be additionally based on the uncorrected two-dimensional x-ray images or the uncorrected sinogram such that the metal objects are present in the three-dimensional tomographic image.

According to the present invention, the artificial intelligence algorithm is trained by using data pairs, where each pair consists of a two-dimensional x-ray image and an associated 2D mask which represents the location of any metal objects in the associated two-dimensional x-ray image. Alternatively, the artificial intelligence algorithm may be trained with a sinogram and an associated 3D mask. The two-dimensional x-ray images are generated through an x-ray source and a detector through a revolution around the patient jaw. The 2D masks or the 3D mask used for the training are obtained through the locations of the metal objects in the two-dimensional x-ray images or the sinogram. One way of obtaining them is by analyzing a three-dimensional tomographic image in which metal artefacts have not been corrected (e.g. by thresholding or other image processing techniques) and subsequently transferring the found masks to the two-dimensional x-ray images or the sinogram (e.g. by means of a forward projection). Alternatively, the 2D masks and/or the 3D mask used in the training step may be manually generated from two-dimensional x-ray images and/or sinograms in which metal artefacts have not be corrected.

According to the present invention, the two-dimensional x-ray images or the sinogram to be obtained is not limited to the entire patient jaw and may also correspond to a part of the patient jaw such as a small volume. Such small volumes may be different in location, size and shape. The metal artefact reduction method may be applied to any small volume even when it is free of metal objects and the patient jaw includes one or more metal object outside the small volume.

The present invention also provides an x-ray dental volume tomography system which has an x-ray unit and a tomographic reconstruction unit. The x-ray unit has an acquisition means for acquiring the two-dimensional x-ray images or the sinogram of at least part of a patient jaw i.e., a small volume, through relatively rotating an x-ray source and a detector around the patient jaw. The part of the patient jaw to be examined can be selected by the user, and accordingly irradiated to prevent overdosing of the patient. The tomographic reconstruction unit also has an image processing means which executes the method according to the present invention for metal artefact reduction in x-ray dental volume tomography.

BRIEF DESCRIPTION OF THE DRAWINGS

In the subsequent description, the present invention will be described in more detail by using exemplary embodiments and by referring to the drawings, wherein FIG. 1—is a tomogram with metal artefacts according to the prior art.

The reference numbers shown in the drawings denote the elements as listed below and will be referred to in the subsequent description of the exemplary embodiments.

1. 2D x-ray image
2. Sinogram
3. Patient
   3a. Patient jaw
4. X-ray source
5. Detector
6. Metal object
   6a. Metal object (outside a small volume (v))
   6b. Metal object (inside the small volume (v))
7. 2D mask
8. 3D tomographic image
9. X-ray unit
V: Part of the patient jaw (3a) or a small volume FIG. 6 shows an x-ray unit (9) according to an embodiment of the present invention. The x-ray unit (9) has an acquisition means for acquiring two-dimensional x-ray images (1) or a sinogram (2) of at least part (V) of a patient jaw (3a) i.e., a small volume, through relatively rotating an x-ray source (4) and a detector (5) around the patient jaw (3a). The x-ray unit (9) is connectable to a tomographic reconstruction unit which has an image processing means which is adapted to execute the method of metal artefact reduction in x-ray dental volume tomography according to the present invention. The x-ray unit (9) and the tomographic reconstruction unit together configure an x-ray dental volume tomography system according to the present invention.

Figure 9A:
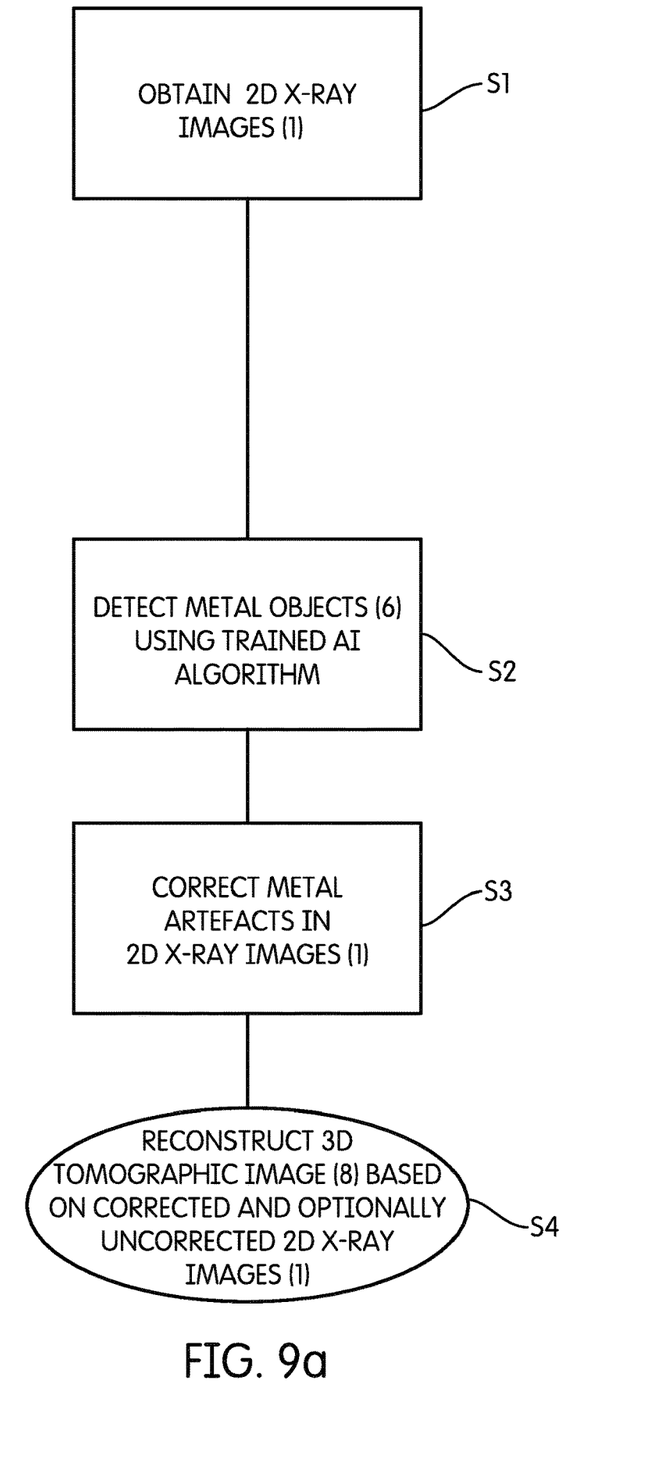
FIG. 9a—is a flowchart showing the steps of a metal artefact reduction method according to a first alternative embodiment of the present invention.

FIG. 9a shows the steps (S1,S2,S3,S4) of the method of metal artefact reduction in x-ray dental volume tomography according to a first alternative embodiment of the present invention.

In a first step (S1), two-dimensional x-ray images (1) or a sinogram (2) of at least part (V) of a patient jaw (3a) is obtained from the acquisition means of the x-ray unit (9). In the second step (S2), the metal objects (6) in the two-dimensional x-ray images (1) or the sinogram (2) are detected by using a trained artificial intelligence algorithm which generates either 2D masks (7) that represent the metal objects (6) in the two-dimensional x-ray images (1) or 3D masks which represent the metal objects (6) in the sinogram (2), respectively. In addition, other 2D masks or 3D masks obtained from a classical algorithm can be optionally used in combination to those generated through the trained artificial intelligence algorithm to optimize the detection. In a third step (S3), the two-dimensional x-ray images (1) or the sinogram (2) are corrected at least by means of the generated 2D masks (7) or the 3D masks respectively. This correction may be performed through classical image processing. Alternatively, the correction may be performed through another trained artificial intelligence algorithm. In step (S4), a three-dimensional tomographic image (8) based on the corrected two-dimensional x-ray images (1) or the corrected sinogram (2) is reconstructed. Alternatively, the reconstruction of the three-dimensional tomographic image (8) may be based on the corrected and the uncorrected two-dimensional x-ray images (1) or the corrected and the uncorrected sinogram (2) so that the metal objects (6), if any, are also shown in the three-dimensional tomographic image (8).

Figure 9B:
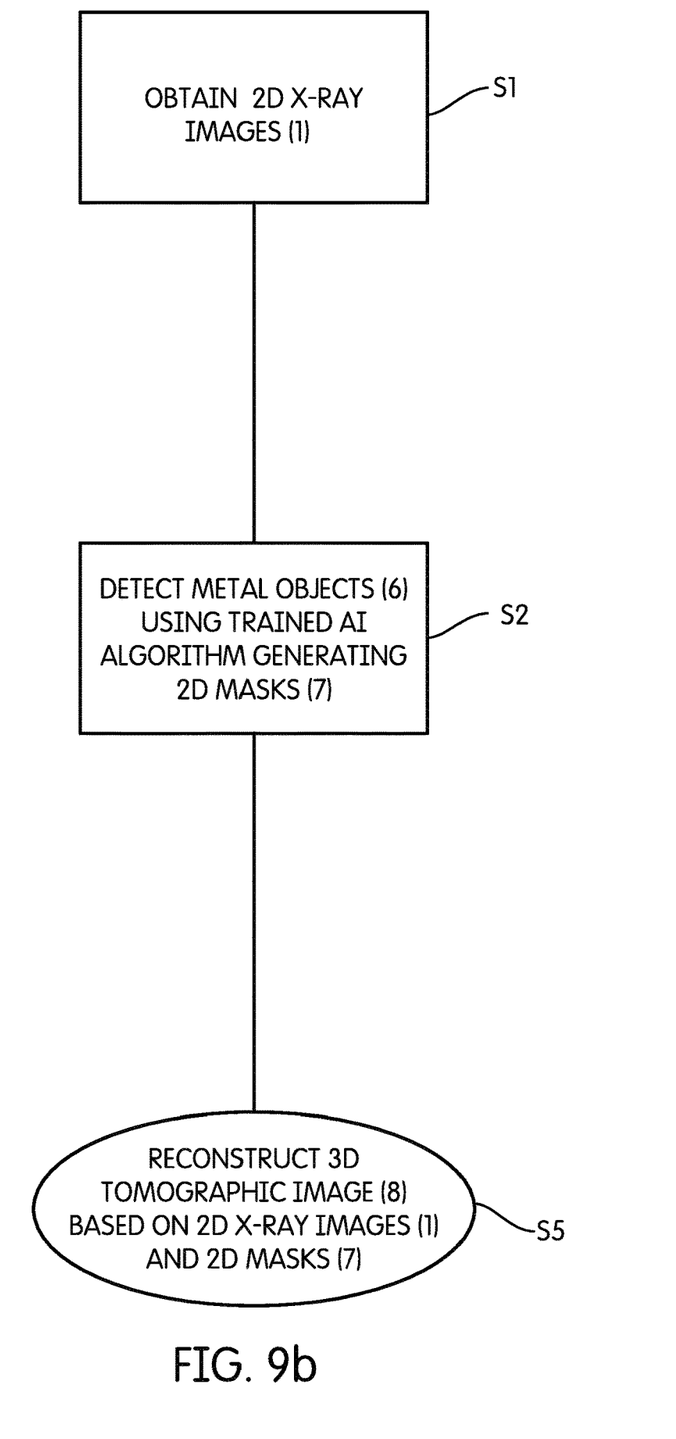
FIG. 9b—is a flowchart showing the steps of a metal artefact reduction method according to a second alternative embodiment of the present invention.

FIG. 9b shows the steps (S1,S2,S5) of the method of metal artefact reduction in x-ray dental volume tomography according to a second alternative embodiment of the present invention. In the second alternative embodiment, the third step (S3) is dispensed with. And the three-dimensional tomographic image (8) is reconstructed respectively based on the two-dimensional x-ray images (1) or the sinogram (2) as originally obtained and the 2D masks (7) or the 3D masks as generated.

Figure 11:
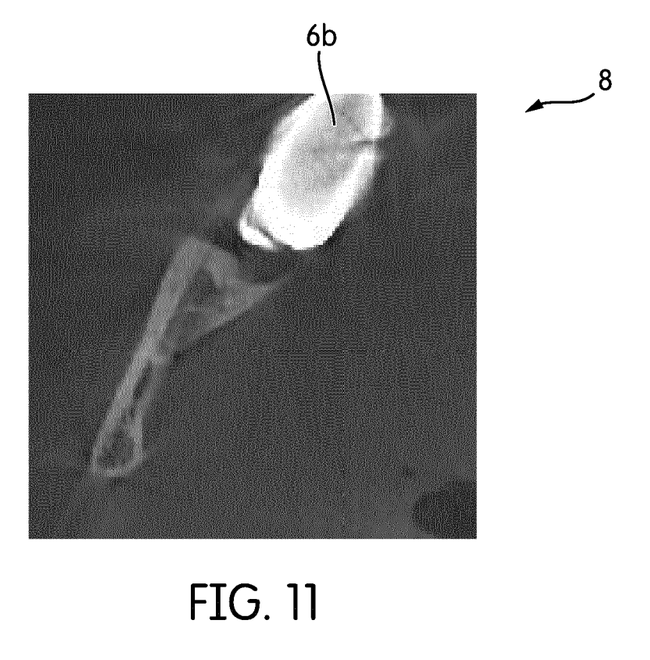
FIG. 11—is a tomogram corresponding to the same section in FIG. 7, reconstructed with the metal artefact reduction method according to the present invention.

For comparison, FIG. 7 shows a tomogram according to the prior art with metal artefacts that are caused by metal objects (6a) outside the reconstructed small volume (V). FIG. 11 shows a tomogram corresponding to the same section in FIG. 7, reconstructed with the metal artefact reduction method according to the present invention.

Figure 10:
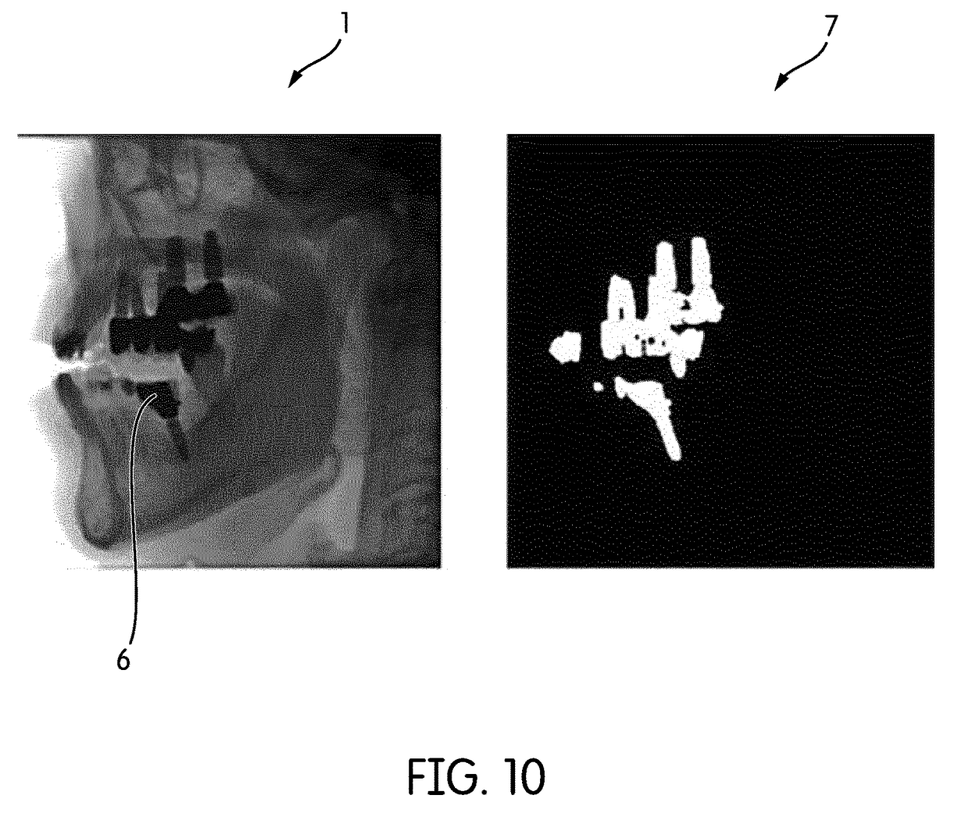
FIG. 10—illustrates a data pair used for training the artificial intelligence algorithm for generating masks according to the present invention, wherein the data pair includes a two-dimensional x-ray image and an associated 2D mask.

The artificial intelligence algorithm is trained by using data pairs. In the subsequent description, the reference signs having a prime denote the elements similar to those without the prime, but which have been used in the training step of the method. Each data pair includes a two-dimensional x-ray image (1') and an associated 2D mask (7') which represents the 2D location of any metal object (6') in the associated two-dimensional image (1'). Alternatively, each data pair includes a sinogram (2') and an associated 3D mask which represents the 3D location of any metal object (6') in the sinogram (2'). Herein the two-dimensional x-ray images (1') and the sinogram (2') of the data pairs correspond, preferably to the entire patient jaw (3a') of an arbitrary patient (3'), which have been generated through an x-ray source (4') and a detector (5') through a relative revolution preferably completely around the patient jaw (3a'). The 2D masks (7') and the 3D mask used in the training step may be obtained by analyzing a three-dimensional tomographic image (8') in which the metal artifacts have not be corrected. For instance, the 2D masks (7') and/or the 3D masks used for the training can be obtained from the prior art method in FIG. 3 as a by-product which result from the analyzing step. Alternatively, the 2D masks (7') and/or the 3D masks used in the training step may be manually generated from two-dimensional images (1') and/or sinograms (2') in which metal artefacts have not be corrected.

In another embodiment, the tomographic reconstruction unit has an input means for retrieving the trained artificial intelligence algorithm for generating the 2D masks (7) and the 3D masks. The input means may be a wireless connection or wired connections that can be connected to a network or the like for data retrieval.

In another embodiment, the acquisition means is adapted to user-selectively acquire two-dimensional x-ray images (1) or the sinogram (2) that corresponds to one of a plurality of different parts (V) of the patient jaw (3a) which have respectively different volumes. The user can select the parts (V) to be irradiated and adjust the size thereof.

In another embodiment, the method is provided in form of a computer-readable program which has codes for causing a computer-based x-ray dental volume tomography system to perform the above-described steps of the metal artefact reduction method in x-ray dental volume tomography.

In another embodiment, the computer-readable program is stored on a computer-readable storage.

The invention claimed is:
1. A method of metal artefact reduction in x-ray dental volume tomography, the method comprising:
   obtaining a sinogram of at least part of a patient jaw, acquired through relatively rotating an X-ray source and a detector around the patient jaw;
   detecting metal objects in the sinogram by using at least a trained artificial intelligence algorithm, without using thresholding or edge detection, to generate 3D masks which represent the metal objects in the sinogram; and
   reconstructing a three dimensional tomographic image based on the sinogram and the 3D masks as generated.
2. The method according to claim 1, further comprising correcting the sinogram by means of the generated 3D masks to form a corrected sinogram, wherein the three dimensional tomographic image is reconstructed based on the corrected sinogram.

3. The method according to claim 2, wherein the sinogram is corrected through classical image processing using thresholding or edge detection.

4. The method according to claim 2, wherein the sinogram is corrected through another trained artificial intelligence algorithm without using thresholding or edge detection.

5. The method according to claim 2, wherein the reconstruction of the three dimensional tomographic image is further based on the corrected sinogram and the uncorrected sinogram.

6. The method according to claim 1, further comprising:
training the artificial intelligence algorithm by using data pairs,
wherein:
each data pair includes a sinogram and an associated 3D mask which represents a location of any metal object in the sinogram;
the sinogram of the data pairs correspond to parts of or the entire patient jaws of one or more patients;
the data pairs have been generated through an x-ray source and a detector or through simulation techniques and cover a plurality of viewing angles; and
at least one of the data pairs comprises at least one metal object.

7. The method according to claim 6, wherein the 3D mask used in the training steps is generated by analyzing a three-dimensional tomographic image in which metal artifacts have not been corrected.

8. The method according to claim 1, wherein:
the sinogram obtained corresponds to a part of the patient jaw which is free of metal objects or includes at least one metal object; and
the remaining part of the patient jaw includes at least one metal object.

9. An x-ray dental volume tomography system comprising:
an x-ray unit comprising an acquisition means adapted to acquire a sinogram of at least part of a patient jaw through relatively rotating an x-ray source and a detector completely around the patient jaw; and
a tomographic reconstruction unit comprising an image processing means adapted to:
detect metal objects in the sinogram acquired by the acquisition means;
detect the metal objects by using a trained artificial intelligence algorithm, without using thresholding or edge detection, which generates 3D masks that represent the metal objects in the sinogram; and
reconstruct a three dimensional tomographic image based on the sinogram and 3D masks as generated.

10. The system according to claim 9, wherein the image processing means is further configured to:
correct the sinogram by means of the generated 3D masks to form a corrected sinogram; and
reconstruct the three dimensional tomographic image based on the corrected sinogram.

11. The system according to claim 10, wherein the image processing means is further adapted to correct the two-dimensional x-ray images or the sinogram through classical image processing using thresholding or edge detection.

12. The system according to claim 10, wherein the image processing means is further adapted to correct the sinogram through another trained artificial intelligence algorithm without using thresholding or edge detection.

13. The system according to claim 10, the image processing means is further adapted to reconstruct the three-dimensional tomographic image based on the corrected sinogram and the sinogram.

14. The system according to claim 9, wherein the tomographic reconstruction unit has an input means for retrieving the trained artificial intelligence algorithm.

15. The system according to claim 9, wherein the acquisition means is adapted to user-selectably and adjustably acquire the sinogram that corresponds to one of a plurality of different user-selectable and adjustable parts of the patient jaw which have different volumes.

16. A non-transitory computer-readable medium storing a program in the medium comprising codes for causing a computer-based x-ray dental volume tomography system to perform a method of:
obtaining a sinogram of at least part of a patient jaw, acquired through relatively rotating an x-ray source and a detector around the patient jaw;
detecting metal objects in the sinogram by using at least a trained artificial intelligence algorithm, without using thresholding or edge detection, to generate 3D masks which represent the metal objects in the sinogram; and
reconstructing a three-dimensional tomographic image based on the sinogram and the 3D masks as generated.

* * * * *

UNITED STATES PATENT AND TRADEMARK OFFICE
CERTIFICATE OF CORRECTION

| | | |
|---|---|---|
| PATENT NO. | : 12,374,003 B2 | Page 1 of 1 |
| APPLICATION NO. | : 17/604045 | |
| DATED | : July 29, 2025 | |
| INVENTOR(S) | : Sarti et al. | |

It is certified that error appears in the above-identified patent and that said Letters Patent is hereby corrected as shown below:

On the Title Page

In item (71), in "Applicants", in Column 1, Line 1, delete "Inc.;" and insert --Inc., York, PA (US);-- therefor In the Claims In Column 6, Line 58, in Claim 1, delete "X-ray" and insert --x-ray-- therefor In Column 7, Line 12, in Claim 5, before "sinogram.", delete "uncorrected"

Signed and Sealed this
Twenty-eighth Day of October, 2025

John A. Squires
*Director of the United States Patent and Trademark Office*